United States Patent [19]

Mèszàros et al.

[11] Patent Number: 4,678,570
[45] Date of Patent: Jul. 7, 1987

[54] PLANAR CENTRIFUGAL CHROMATOGRAPHY DEVICE

[75] Inventors: Sàndor Mèszàros; Gisela Verzàr-Petri; Klara Nyiredy-Mikita; Ernö Tyihàk, all of Budapest, Hungary; Szabolcs Nyiredy, Zurich, Switzerland; Beat Meier, Brütten, Switzerland; Otto Sticher, Zurich, Switzerland; Karin Dallenbach-Toelke, Küsnacht, Switzerland

[73] Assignee: Petazon Inc., Zug, Switzerland

[21] Appl. No.: 849,939

[22] Filed: Apr. 9, 1986

[30] Foreign Application Priority Data

Apr. 15, 1985 [CH] Switzerland .......................... 1588/85
Apr. 15, 1985 [CH] Switzerland .......................... 1589/85

[51] Int. Cl.$^4$ ............................................. B01D 15/08
[52] U.S. Cl. .............................. 210/198.2; 210/198.3; 210/657; 210/658
[58] Field of Search .................... 210/657, 658, 198.2, 210/656, 198.3

[56] References Cited

U.S. PATENT DOCUMENTS 2,986,280  5/1961  Magnuson .......................... 210/657
3,113,103  12/1963  Lowery .............................. 210/657
3,617,557  11/1971  Giltrow ............................. 210/657
4,139,458  2/1979  Harrison ............................ 210/657
4,422,941  12/1983  Vaughan ............................ 210/657

FOREIGN PATENT DOCUMENTS

WO85/04594  10/1985  PCT Int'l Appl. ................. 210/657

Primary Examiner—Ernest G. Therkorn
Attorney, Agent, or Firm—Flynn, Thiel, Boutell & Tanis

[57] ABSTRACT

A planar centrifugal chromatography device includes a chamber (2), and a rotor (3) arranged therein, driven by a motor (12) and serving as a separating element. The rotor has a supporting plate (15) with an adsorbing medium (4) provided thereon. A collecting device (5) is arranged near the outer edge of the rotor, but within the chamber.

The characteristics of the invention include the collecting device (5) and the rotor (3) being mounted on a common shaft (10) and each individual point of a wall of the collecting device (5) being farther away from the axis of rotation (14) than the point of the adsorbing medium (4) which is farthest from the axis of rotation (14), and include the distances of individual points on the wall of the collecting device (5), measured from the axis of rotation (14), varying. At each point on the collecting device which is farther from the axis than two points which are adjacent to it, there is arranged an output opening (6) which is connected by a discharge channel (7) to a hollow part of the shaft (10) of the rotor (3), and wherein a stationary discharge element (8), for example a pump, is connected to the shaft (10).

7 Claims, 5 Drawing Figures

PLANAR CENTRIFUGAL CHROMATOGRAPHY DEVICE

FIELD OF THE INVENTION

The invention relates to a planar centrifugal chromatography device and, more particularly, to such a device having a chamber with a rotating rotor therein which constructed as a chromatographical separating element and which has a support plate thereon and an annular adsorbing medium arranged on the support plate, and a collecting device arranged very close to the outer edge of the rotor but within the chamber.

BACKGROUND OF THE INVENTION

U.S. Pat. No. 4 139 458 describes a planar centrifugal chromatography device in which a rotor constructed as a flat disk and made of glass is arranged within a chamber which is inclined to the horizontal. The adsorbing medium is arranged on the upper side of the rotor. An inner wall of the chamber, which is inclined toward the axis of the rotor at an angle of less than 90° with respect to the upper side of the rotor, forms the collecting device. The solvent is introduced onto the upper surface of the adsorbing medium near the shaft of the rotor. The solvent flows through the adsorbing medium under the action of centrifugal force, which causes the chromatographical separation. The solvent exits from the adsorbing medium, together with the separated substance, at the edge of the circular glass disk and moves, due to the centrifugal force, into the collecting device which is constructed in the stationary chamber. The solvent flows, under the action of gravity, to the lowermost point of the inclined chamber, where it is removed from the device through an output opening.

A disadvantage of this solution is that the solvent, together with the separated substances contained in the solvent, moves from the higher points of the chamber—due to the relatively large distance and the weak driving force of gravity — only slowly into the output opening. The solvent particles which move into the collecting channel near the output opening leave the device more quickly. Thus, there exists the danger of remixing between the already separated particles, which causes the separation accomplished in the adsorbing medium to become substantially worse.

A further disadvantage of the known device is that the great turbulence which occurs due to the rotor, which rotates in the vapor space, does not permit the construction of a vapor space with a defined composition. This has the result that a part of the solvent does not flow through the adsorbing medium, but instead evaporates and is removed — not fulfilling its task. This fact reduces the repeatability and efficiency of the separation. Because of these deficiencies, it is not possible to carry out analytic (non preparatory) chromatography with the known device.

A further disadvantage in the design according to U.S. Pat. No. 4 139 458 is that the adsorbing medium is glued on the glass plate which forms the rotor, or is secured thereon. Thus, only an adhesive adsorbing medium can be used.

Tests have been made to overcome this disadvantage, namely with a disk in which the adsorbing medium is arranged between two parallel circular glass plates. (See the device of Hitachi Corp.) The disadvantage of this solution is that a cross section of the adsorbing medium which is vertical with respect to the radius is not constant, that is, the force due to inertia changes with the distance from the centerpoint, which results in a strip enlargement.

In another known device (PCT WO 85/04594 and HRC & CC, Edition 8/1985/Pages 53, 132), the solvent is applied to the center part of a rotatable rotor inclined at an angle to the horizontal with the help of a feed device which is movable and adjustable between the centerpoint and the edge of the rotor. After the chromatographic separation is finished, the solvent is removed with the help of an annular stationary collecting device. In this solution, there again exists the danger of remixing, that is, the efficiency of the separation accomplished in the adsorbing medium is through this discharge substantially reduced.

A purpose of the invention is to create a planar centrifugal chromatography device in which the discharge of the solvent can be accomplished quickly and without any danger of remixing.

SUMMARY OF THE INVENTION

This purpose is attained in a planar centrifugal chromatography device of the abovementioned type in which the collecting device and the rotor are mounted fixedly on a common shaft and every individual inner point of an inner surface on the catching device is farther from the axis of rotation than the point on the adsorbing medium of the rotor which is the farthest from the axis of rotation, the distance of the individual points on the inner surface of the catching device as measured from the axis of rotation varying, wherein at each point of the catching device which is farther from the axis than two adjacent points there is arranged an output opening which is connected to an axially extending hollow part of the shaft of the rotor through a discharge channel, the device having a stationary discharge element which is connected to the hollow part of the shaft.

The catching device is advantageously designed as a collecting channel, in which the distance of the individual points of the collecting channel changes symmetrically in relationship to the axis of rotation of the rotor and, at the most remote point of the collecting channel, there are arranged respective output openings, in particular at least two and advantageously an even number of output openings.

An advantage of the inventive planar centrifugal chromatography device is that the solvent can be discharged much more quickly from it than from known devices, because the collecting device rotates with the rotor, which causes during discharge of the solvent the utilization of centrifugal force instead of gravity, the centrifugal force being much greater than the gravitational force. The solvent is thereby centrifuged from the separating element radially outwardly and against the collecting device having the collecting channel, from which it is removed for further use by means of the discharge element through the output opening, the discharge channel and the hollow part of the drive shaft. The great centifugal force results in addition in the possibility of using an adsorbing media having an efficiency which is high and a core diameter which is small. From the fact that, during the discharge of the solvent, centrifugal force and not the gravitational force is utilized, there follows still the further advantage that the rotor can be arranged horizontally and need not necessarily be inclined, which simplifies the arrangement of the device.

The provision of several output openings has the result that the discharge of the solvent is accelerated. The quick discharge reduces the danger of remixing, which results in an improvement of efficiency.

The use of a collecting device which rotates with the rotor results in the possibility to cover the adsorbing medium, through which a vapor space of a defined composition is created above the adsorbing medium, which is the condition for analytic use.

An advantageous embodiment of the chromatographic separating element, which includes a rotor, a lower support plate, an upper cover plate and an adsorbing medium disposed between the two plates, has the inventive characteristics that, between the support plate and cover plate, there exists a gap in which the adsorbing medium is annularly arranged, that the height of the gap changes, starting from the axis of rotation of the separating element and in the direction of a radius, according to the equation $$h = \frac{K}{a + b \cdot r + c \cdot r^2},$$

where K, a, b and c, are predeterminable constants, and that a cover filter is arranged in the gap near the outer circumference thereof.

The height of the gap is advantageously reduced in a reverse relationship to a distance measured from the axis of rotation of the separating element in the direction of a radius, that is, an imaginary annular cross-sectional surface of the gap which is normal to the direction of the radius has a constant area for each length of the radius, that is $h = K/r$.

If the cross section of the gap is in the direction of the radius, then the requirement for column chromatography is met, namely that the cross-sectional area of the adsorbing medium in a direction normal to the flow direction of the solvent must be strictly constant. From this the advantage that the fillers which exist in column chromatography can be used without binding agents. A further advantage of this solution is that the filling of the column can be reproduced easily and dependably.

The embodiment in which the height of the gap changes according to the equation $h = k/r^2$, namely where the force due to inertia along the radius as measured from the axis of the separating element is constant, is advantageous because the flow speed of the solvent is constant through this, and thus the possibility results to adjust to a flow speed which is the optimum flow speed from a standpoint of separation.

In another embodiment, the separating element is arranged rotatably about the axis, and annular channels for introducing the solvent are constructed in one of the plates concentric with respect to the axis, the ends of the channels adjacent the adsorbing medium being covered with a filter plate. This embodiment has the advantage that the solvent can be introduced between the axis and the edge of the separating element at any point or points, which can influence the efficiency of the separation.

BRIEF DESCRIPTION OF THE DRAWINGS

The invention will be described in greater detail hereinafter in connection with the drawings, which are purely diagrammatic and in which.

DETAILED DESCRIPTION

The basic structure of a chromatography device has become known from various patents and many publications. The main parts of such a device will be discussed hereinafter.

Figure 1:
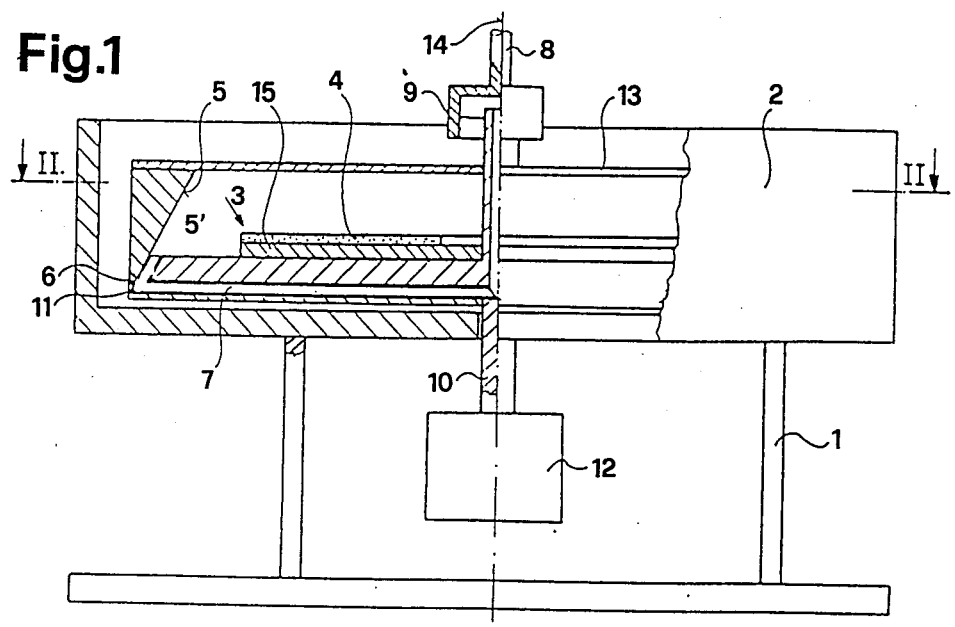
FIG. 1 is a side view of the inventive planar centrifugal chromatography device, partially in cross section.
Figure 2:
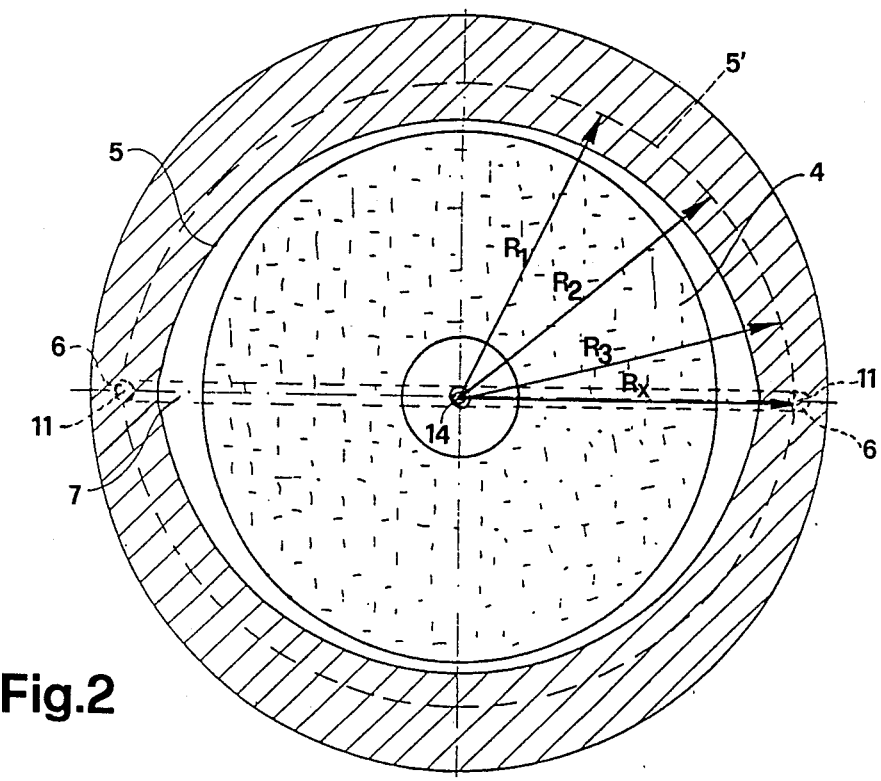
FIG. 2 is a cross-sectional view taken along the line II—II in FIG. 1.

The inventive planar centrifugal chromatography device according to FIGS. 1 and 2 includes a conventional chamber 2 which is arranged horizontally on a frame 1. A rotor 3 is arranged in the chamber 2, which rotor can be rotated about a shaft 10 with the help of a motor 12. The speed of the motor 12 can be varied and lies between 50 and 3,600 t/min.

The rotor 3 is also arranged horizontally, and contains an adsorbing medium 4 which rotates with the rotor 3. The rotor can be constructed in a common manner, and the adsorbing medium 4 is then applied as a circular ring onto a circular glass disk 15 which serves as a support plate. However, it is also possible to use a rotor 3 in which the adsorbing medium 4 is provided between two disks, namely between a support plate and a cover plate, wherein one disk can be constructed of a transparent material.

A collecting device 5 is arranged on the outer circumferential edge of the rotor 3 within the chamber 2, which device 5 is mounted on the shaft 10 so that it turns with the rotor 3 and the adsorbing medium 4.

The collecting device 5 can be constructed with a collecting surface on its inside which is inclined, to define a collecting channel 5'.

Each individual point of the collecting device 5 having the collecting channel 5' is on the one hand farther removed from the axis of rotation 14 of the chromatography device as shown in FIG. 2 by radi $R_1$, $R_2$, $R_3$... , than the point $R_x$ of the adsorbing medium 4, which point $R_x$ is the farthest from the axis of rotation 14. The distances $R_1$, $R_2$, $R_3$... of individual points on the collective device 5, measured from the axis of rotation 14, can differ from each on the other hand. At each point 11 on the collecting device 5 or the collecting channel 5' which is farther from the axis 14 than two points which are adjacent to it, there is constructed an output opening 6. The output openings 6 and a hollow part of the shaft 10 of the rotor 3 are connected by radially extending discharge channels 7. A stationary discharge element 8, for example a suction pump with the interpositioning of a rotating seal 9 such as a retaining ring, is connected to the shaft 10. The space in the chamber with the separating element and the catching device can also be under a vacuum.

The collecting device 5 has, in the illustrated exemplary embodiment, a collecting channel 5' in which the distance of the individual points of the collecting channel 5' from the axis 14 changes symmetrically in relationship to the axis of rotation 14 of the rotor 3, and one output opening 6 is constructed at each of the farthest removed points 11 of the collecting channel 5'. Advantageously there are at least two, and preferably an even number of, output openings 6 which are arranged symmetrically with respect to the axis of rotation 14. Of course, it is also possible to arrange the output openings 6 asymmetrically and in uneven numbers.

Viewed from the standpoint of the invention, it is only important that one output opening 6 be provided at each point of the collecting channel 5' which is farther from the axis 14 than two points of the collecting device which are adjacent to it.

A lid 13 can be arranged above the adsorbing medium, which lid 13 rotates with the rotor 3. The lid 13 may consist of a transparent, translucent or opaque material, for example of glass, metal or plastic. In choosing the lid material, there exists only a single requirement, namely that the solvent or its vapor not attack the lid material. The lid 13 hermetically closes at its edge the space which exists above the adsorbing medium 4, and in this manner secures the stability of the vapor space which exists above the adsorbing medium.

The inventive planar centrifugal chromatography device according to FIGS. 1 and 2 operates as follows:

The mixture which is to be separated is applied on the center part of the rotating rotor 3 and is separated by an elution which is created with the help of centrifugal force in such a manner that the mixture flows through the adsorbing medium 4.

The separated solution flows, under the action of the centrifugal force of the rotating part which includes the support plate 15, the medium 4 and the catching device 5, into the output openings 6 arranged at the points 11 of the collecting device 5 farthest from the axis 14, and moves through these and through the discharge channels 7 into the shaft 10. On the shaft 10 there is arranged, with the help of a seal 9 which for example is a retaining ring, the stationary discharge element 8, for example a pump or an excess pressure or vacuum arrangement, through which the solvent is discharged.

Figure 3:
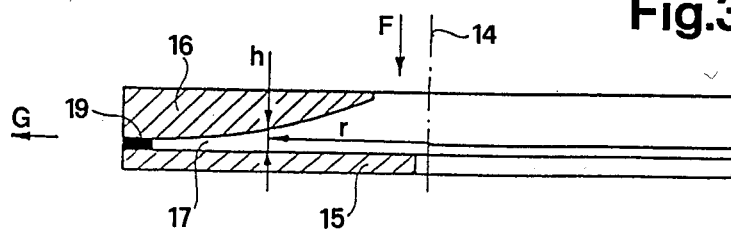
FIG. 3 is a side view, partially in cross section, of the inventive separating element in an unfilled condition.
Figure 4:
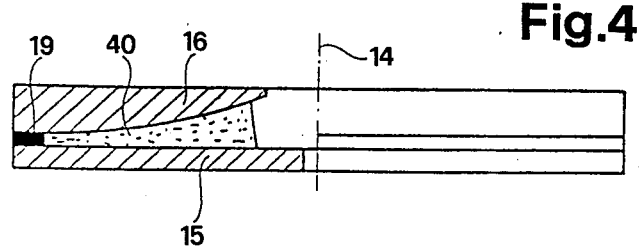
FIG. 4 is a view similar to FIG. 3 which illustrates the same separating element in a condition in which it is filled with an adsorbing medium.

FIGS. 3 and 4 illustrate a modification of the separating element, which can be inserted into the device according to FIGS. 1 and 2 in the place of the rotor 3. A lower support plate 15 and an upper cover plate 16 are mounted on a shaft having an axis of rotation 14. A gap 17 exists between the two plates, in which gap there is arranged an annular adsorbing medium 40. The height h of the gap 17 changes, from the axis of rotation 14 of the separating element in the direction of the radius r, according to the equation $$h = \frac{K}{a + b \cdot r + c \cdot r^2},$$

where K, a, b and c are constants. Near the outer circumference of the separating element, there is arranged an annular cover filter 19, which blocks the outer end of the gap 17 and holds in the gap the adsorbing medium 40 which has been moved into the gap, wherein the cover filter 19 lets the solvent through.

The height h of the gap which exists between the lower support plate 15 and the upper cover plate 16 changes in the direction of the radius r measured outwardly from the axis 14 according to the equation $h = K/r$, if $a = c = 0$ and $b = 1$. The cross-sectional surface area of an entire ring at any radius r of the gap 17, which cross-sectional surface is imaginary and extendes perpendicular to the direction of the radius, is in this case constant and is only dependent on the coefficient K.

The height h of the gap 17 which exists between the lower support plate 15 and the upper cover plate 16 can also change in the direction of the radius r measured outwardly from the axis 14 according to the equation $h = k/r^2$, if $a = b = 0$ and $c = 1$. The force due to inertia along the radius r is in this case constant.

Figure 5:
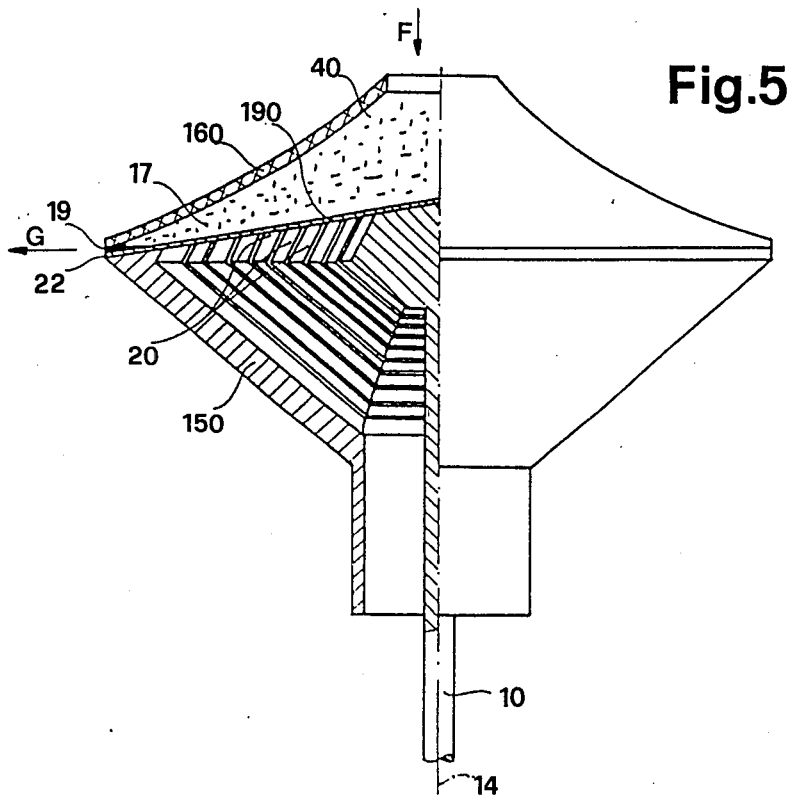
FIG. 5 is a side view, partially in cross section, of a further embodiment of the separating element in which concentric annular channels are provided.

FIG. 5 illustrates a further modification of the separating element, which is rotatable about the axis 14 and in which, either in a support plate 150 or in a cover plate 160, there are arranged annular channels 20 which are concentric to the axis 14. The channels 20 are used to introduce solvent at various points. The adsorbing medium 40 is provided in the gap 17 between the support plate 150 and cover plate 160. The ends of the channels 20 which are adjacent the adsorbing medium 40 are covered with a filter plate 190, so that the adsorbing medium 40 does not penetrate into the channels 20.

The separating elements which are described in connection with FIGS. 3 to 5 are used in the following manner:

The solvent is introduced near the axis 14 in the direction of the arrow F and flows through the adsorbing medium 4 in the direction of the radius r to the outside. The chromatographical separation occurs in the meantime. The solvent leaves the separating element in the direction of the arrow G.

The solvent flows through the adsorbing medium 40 under the action of centrifugal force if the separating element is rotated in such a manner that the shaft 10 is driven in a conventional manner with an electric motor, or the separating element can be used stationarily and the solvent driven pneumatically through the adsorbing medium 40. The flow through the adsorbing medium can in this case also occur in a reverse direction, that is, the solvent can be introduced at the edge 22 of the separating element and can be removed near the axis 14.

If a separating element according to FIG. 5 is used, in which concentric annular channels 20 are provided, there exists the possibility to introduce the solvent between the axis 14 and the edge 22 of the separating element at any point or points, through which the efficiency of the separation can be influenced.

The embodiments of the invention in which an exclusive property or privilege is claimed are defined as follows:

1. In a planar centrifugal chromatography device which includes a chamber with a rotating rotor therein constructed as a chromatographical separating element having a support plate, having an annular adsorbing medium arranged on the support plate, and having a collecting device arranged very close to the outer edge of the rotor within the chamber, the improvement comprising wherein the collecting device and the rotor are mounted fixedly on a common shaft and every individual point on an inner surface of the collecting device is farther from the axis of rotation than the point of the adsorbing medium of the rotor which is the farthest from the axis of rotation, wherein the distances of the individual points on the inner surface of the collecting device from the axis of rotation vary, and at each point on the collecting device which is farther from the axis than two adjacent points there is arranged an output opening which is connected to an axially extending hollow part of the shaft of the rotor through a discharge channel, and wherein the device has a stationery discharge element which is connected to the hollow part of the shaft.

2. Planar centrifugal chromatography device according to claim 1, wherein the collecting device has a collecting channel in which the distances of the individual points on the inner surface of the collecting channel change symmetrically in relationship to the axis of rotation of the rotor, and wherein at the most remote points of the collecting channel there are arranged respective output openings, in particular at least two and advantageously an even number of output openings.

3. Planar centrifugal chromatography device according to claim 1, wherein above the absorbing medium there is arranged a lid which rotates with said adsorbing medium and which is hermetically secured at its edge with respect to the collecting device.

4. Planar centrifugal chromatography device according to claim 1, wherein the rotor, which is constructed as a chromatographic separating element, includes a lower support plate, an upper cover plate and an adsorbing medium which is disposed between the two plates, wherein between the support plate and cover plate there is provided a gap in which the adsorbing medium is concentrically arranged, wherein the height of the gap changes, starting from the axis of rotation of the separating element and in the direction of a radius, according to the equation.

$$h = \frac{K}{a + b \cdot r + c \cdot r^2},$$

where K, a, b and c are predeterminable constants, and wherein a cover filter is arranged in the gap near the outer circumference thereof.

5. Planar centrifugal chromatography device according to claim 4, wherein the height of the gap decreases in a reverse relationship to a distance which is measured starting from the axis of rotation of the separating element and in the direction of a radius, that is, an area of an imaginary annular cross-sectional surface of the gap which is perpendicular to the direction of the radius is constant for each radius length, that is, $h = K/r$.

6. Planar centrifugal chromatography device according to claim 4, wherein the height of the gap changes according to the equation $h = K/r^2$, that is, the force due to inertia along a radius measured from the axis of rotation of the separating element is constant.

7. Planar centrifugal chromatography device according to claim 4, wherein the separating element is arranged rotatably about the axis of rotation and has in one of the support and cover plates or annular channels concentric with respect to the axis of rotation for introducing the solvent, and wherein the ends of the channels which are adjacent the adsorbing medium are covered with a filter plate.

* * * * *